United States Patent [19]

Seligman et al.

[11] Patent Number: 5,271,397
[45] Date of Patent: Dec. 21, 1993

[54] MULTI-PEAK SPEECH PROCESSOR

[75] Inventors: Peter M. Seligman, Essendon; Richard C. Dowell, North Eltham; Peter J. Blamey, Waverley, all of Australia

[73] Assignees: Cochlear Pty. Ltd., Parkville; The Univ. of Melbourne, Victoria, both of Australia

[21] Appl. No.: 808,428

[22] Filed: Dec. 16, 1991

Related U.S. Application Data

[62] Division of Ser. No. 577,657, Sep. 4, 1990, Pat. No. 5,095,904.

[30] Foreign Application Priority Data

Sep. 8, 1989 [AU] Australia ............... PJ6249

[51] Int. Cl.[5] .................. A61N 1/00; H04R 25/00; A61F 2/18; A61F 2/54
[52] U.S. Cl. ............................ 607/137; 623/10; 623/66
[58] Field of Search ............... 623/10, 11, 66; 128/642, 784, 789, 420.5, 420.6

[56] References Cited

U.S. PATENT DOCUMENTS

| | | | |
|---|---|---|---|
| 3,449,768 | 6/1969 | Doyle | 3/1 |
| 3,751,605 | 8/1973 | Michelson | 197/107 R |
| 3,752,939 | 8/1973 | Bartz | 179/107 R |
| 4,063,048 | 12/1977 | Kissiah, Jr. | 179/107 R |
| 4,207,441 | 6/1980 | Ricard et al. | 179/107 R |
| 4,267,410 | 5/1981 | Forster et al. | 179/107 BC |
| 4,284,856 | 8/1981 | Hochmair et al. | 179/107 E |
| 4,357,497 | 11/1982 | Hochmair et al. | 179/107 E |
| 4,400,590 | 8/1983 | Michelson | 128/420.6 |
| 4,419,995 | 12/1983 | Hochmair et al. | 128/419 R |
| 4,499,339 | 2/1985 | Richard | 179/107 FD |
| 4,515,158 | 5/1985 | Patrick et al. | 128/419 R |
| 4,532,930 | 8/1985 | Crosby et al. | 128/419 R |
| 4,592,359 | 6/1986 | Galbraith | 128/419 R |
| 4,593,696 | 6/1986 | Hochmair et al. | 128/419 R |
| 4,611,598 | 9/1986 | Hortmann et al. | 128/419 R |
| 4,686,765 | 8/1987 | Byers et al. | 128/420.6 X |
| 4,813,417 | 3/1989 | Soli et al. | 128/420.5 |
| 4,832,051 | 5/1989 | Jawik et al. | 128/420.6 X |
| 4,918,745 | 4/1990 | Hutchison | 128/789 X |
| 4,944,301 | 7/1990 | Widin et al. | 128/420.6 |
| 4,947,844 | 8/1990 | McDermott | 128/421 |
| 5,061,282 | 10/1991 | Jacobs | 128/420.6 X |

FOREIGN PATENT DOCUMENTS

| | | | |
|---|---|---|---|
| 1819483 | 8/1983 | Australia . | |
| 0001915 | 5/1979 | European Pat. Off. | 623/10 |

OTHER PUBLICATIONS

M. M. Merzenich et al., "Cochlear Implant Prosthesis: Strategies and Progess", *Annals of Biomedical Engineering*, vol. 8, pp. 361-368 (1980).

O. Ozdamar et al., "Tactile Vocoders for the Deaf", *IEEE Engineering in Medicine and Biology*, pp. 37-42, (Sep. 1987).

S. A. Shamma-Donoghue et al., "Thin Film Multielectrode Arrays for a Cochlear Prosthesis", *IEEE Transactions on Electron Devices*, vol. ED-29, No. 1, pp. 136-144 (Jan. 1982).

*Primary Examiner*—David Isabella
*Assistant Examiner*—Elizabeth M. Burke
*Attorney, Agent, or Firm*—Gottlieb, Rackman & Reisman

[57] ABSTRACT

An improved pulsatile system for a cochlear prosthesis is disclosed. The system employs a multi-spectral peak coding strategy to extract a number, for example five, of spectral peaks from an incoming acoustic signal received by a microphone. It encodes this information into sequential pulses that are sent to selected electrodes of a cochlear implant. The first formant (F1) spectral peak (280–1000 Hz) and the second formant (F2) spectral peak (800–4000 Hz) are encoded and presented to apical and basal electrodes, respectively. F1 and F2 electrode selection follows the tonotopic organization of the cochlea. High-frequency spectral information is sent to more basal electrodes and low-frequency spectral information is sent to more apical electrodes. Spectral energy in the regions of 2000–2800 Hz, 2800–4000 Hz, and above 4000 Hz is encoded and presented to three fixed electrodes. The fundamental or voicing frequency (F0) determines the pulse rate of the stimulation during voiced periods and a pseudo-random aperiodic rate determines the pulse rate of stimulation during unvoiced periods. The amplitude of the acoustic signal in the five bands determines the stimulus intensity.

4 Claims, 7 Drawing Sheets

ANATOMICAL ARRANGEMENT

COCHLEA IN CROSS-SECTION

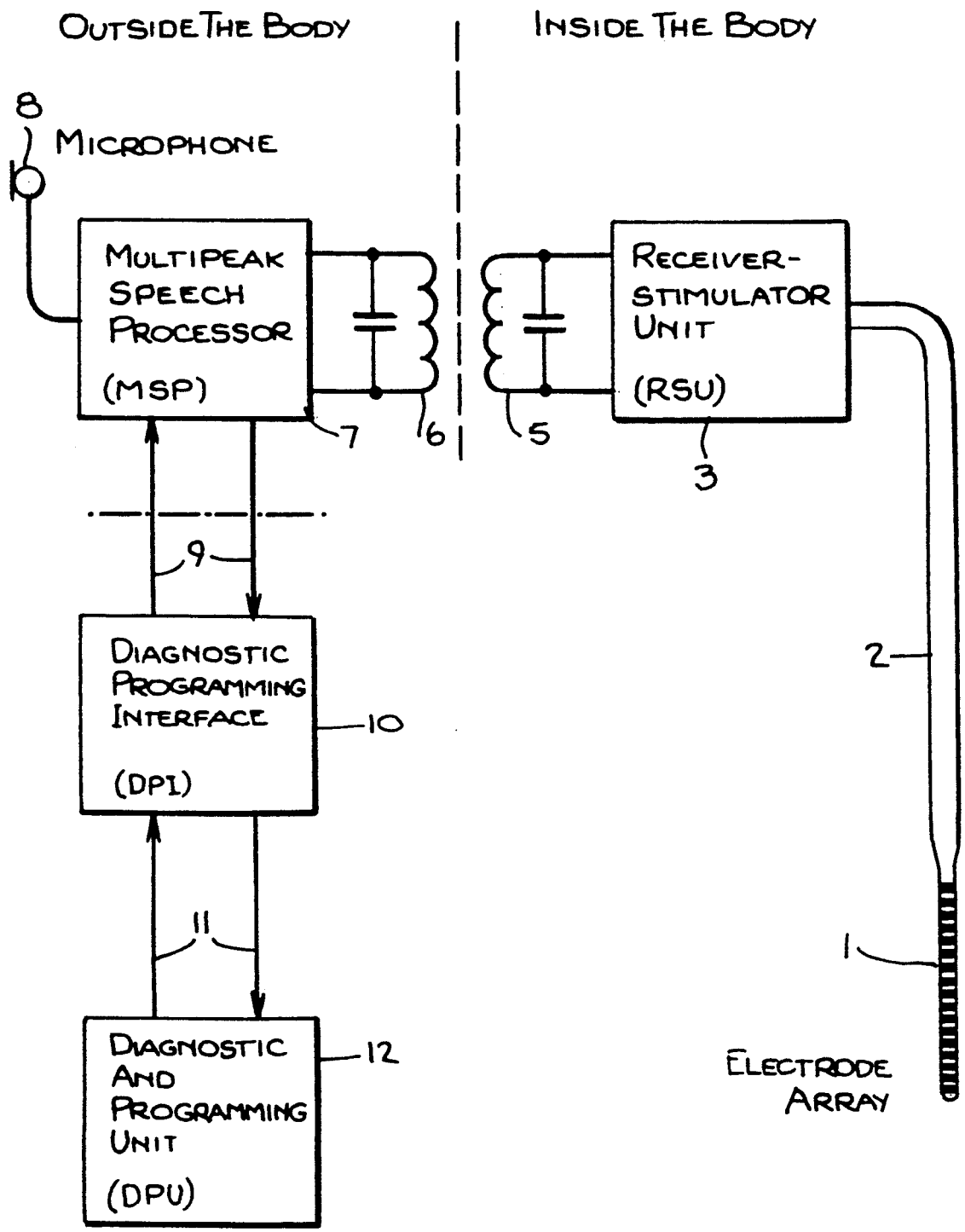

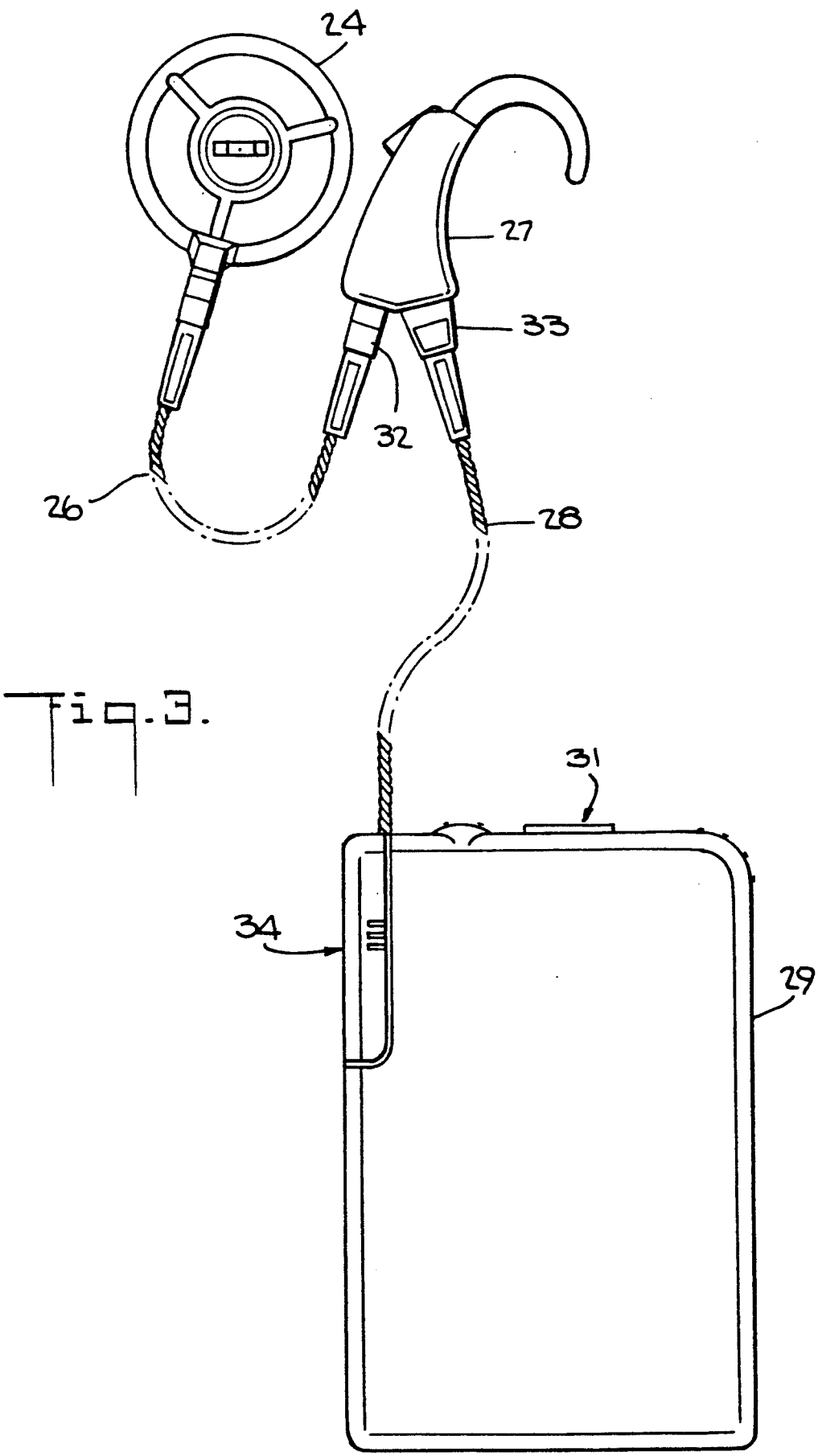

ACTIVE ELECTRODE STIMULUS CURRENT

MPEAK STRATEGY - VOICED SOUNDS

MPEAK STRATEGY - UNVOICED SOUNDS

ELECTRICAL STIMULATION PATTERNS FOR THE MPEAK STRATEGY

STANDARD LOUDNESS GROWTH FUNCTION FOR THE WSP

MULTI-PEAK SPEECH PROCESSOR

This is a division of application Ser. No. 577,657, filed Sep. 4, 1990, now U.S. Pat. No. 5,095,904.

TECHNICAL FIELD

This invention relates to pulsatile type multi-channel cochlear implant systems for the totally or profoundly deaf.

Pulsatile multi-channel cochlear implant systems generally include a cochlear implant, an external speech processor, and an external headset. The cochlear implant delivers electrical stimulation pulses to an electrode array (e.g., 22 electrodes) placed in the cochlea. The speech processor and headset transmit information and power to the cochlear implant.

The speech processor operates by receiving an incoming acoustic signal from a microphone in the headset, or from an alternative source, and extracting from this signal specific acoustic parameters. Those acoustic parameters are used to determine electrical stimulation parameters, which are encoded and transmitted to the cochlear implant via a transmitting coil in the headset, and a receiving coil forming part of the implant.

In many people who are profoundly deaf, the reason for deafness is absence of, or destruction of, the hair cells in the cochlea which transduce acoustic signals into nerve impulses. These people are thus unable to derive any benefit from conventional hearing aid systems, no matter how loud the acoustic stimulus is made, because it is not possible for nerve impulses to be generated from sound in the normal manner. Cochlear implant systems seek to bypass these hair cells by presenting electrical stimulation to the auditory nerve fibers directly, leading to the perception of sound in the brain. There have been many ways described in the past for achieving this object, running from implantation of electrodes in the cochlea connected to the outside world via a cable and connector attached to the patient's skull, to sophisticated multichannel devices communicating with an external computer via radio frequency power and data links.

The invention described herein is particularly suited for use in a prosthesis which comprises a multichannel electrode implanted into the cochlea, connected to a multichannel implanted stimulator unit, which receives power and data from an externally powered wearable speech processor, wherein the speech processing strategy is based on known psychophysical phenomenon, and is customized to each individual patient by use of a diagnostic and programming unit. One example of such a prosthesis is the one shown and described in U.S. Pat. No. 4,532,930 to Crosby et al., entitled "Cochlear Implant System for an Auditory Prosthesis."

In order to best understand the invention it is necessary to be aware of some of the physiology and anatomy of human hearing, and to have a knowledge of the characteristics of the speech signal. In addition, since the hearing sensations elicited by electrical stimulation are different from those produced by acoustic stimulation in a normal hearing person, it is necessary to discuss the psychophysics of electrical stimulation of the auditory system. In a normal hearing person, sound impinges on the ear drum, as illustrated in FIG. 1, and is transmitted via a system of bones called the ossicles, which act as levers to provide amplification and acoustic impedance matching to a piston, or membrane, called the oval window, which is coupled to the cochlea chamber.

The cochlear chamber is about 35 mm long when unrolled and is divided along most of its length by a partition. This partition is called the basilar membrane. The lower chamber is called the scala tympani. An opening at the remote end of the cochlea chamber communicates between the upper and lower halves thereof. The cochlea is filled with a fluid having a viscosity of about twice that of water. The scala tympani is provided with another piston or membrane called the round window which serves to take up the displacement of the fluid.

When the oval window is acoustically driven via the ossicles, the basilar membrane is displaced by the movement of fluid in the cochlea. By the nature of its mechanical properties, the basilar membrane vibrates maximally at the remote end or apex of the cochlea for low frequencies, and near the base or oval window thereof for high frequencies. The displacement of the basilar membrane stimulates a collection of cells called the hair cells situated in a special structure on the basilar membrane. Movements of these hairs produce electrical discharges in fibers of the VIIIth nerve, or auditory nerve. Thus the nerve fibers from hair cells closest to the round window (the basal end of the cochlea) convey information about high frequency sound, and fibers more apical convey information about low frequency sound. This is referred to as the tonotopic organization of nerve fibers in the cochlea.

Hearing loss may be due to many causes, and is generally of two types. Conductive hearing loss occurs when the normal mechanical pathways for sound to reach the hair cells in the cochlea are impeded, for example by damage to the ossicles. Conductive hearing loss may often be helped by use of hearing aids, which amplify sound so that acoustic information does reach the cochlea. Some types of conductive hearing loss are also amenable to alleviation by surgical procedures.

Sensorineural hearing loss results from damage to the hair cells or nerve fibers in the cochlea. For this type of patient, conventional hearing aids will offer no improvement because the mechanisms for transducing sound energy into nerve impulses have been damaged. It is by directly stimulating the auditory nerve that this loss of function can be partially restored.

In the system described herein, and in some other cochlear implant systems in the prior art, the stimulating electrodes are surgically placed in the scala tympani, in close proximity to the basilar membrane, and currents that are passed between the electrodes result in neural stimulation in groups of nerve fibers.

The human speech production system consists of a number of resonant cavities, the oral and the nasal cavities, which may be excited by air passing through the glottis or vocal cords, causing them to vibrate. The rate of vibration is heard as the pitch of the speaker's voice and varies between about 100 and 400 Hz. The pitch of female speakers is generally higher than that of male speakers.

It is the pitch of the human voice which gives a sentence intonation, enabling the listener, for instance, to be able to distinguish between a statement and a question, segregate the sentences in continuous discourse and detect which parts are particularly stressed. This together with the amplitude of the signal provides the so-called prosodic information.

Speech is produced by the speaker exciting the vocal cords, and manipulating the acoustic cavities by movement of the tongue, lips and jaw to produce different sounds. Some sounds are produced with the vocal cords excited, and these are called voiced sounds. Other sounds are produced by other means, such as the passage of air between teeth and tongue, to produce unvoiced sounds. Thus the sound "Z" is a voiced sound, whereas "S" is an unvoiced sound; "B" is a voiced sound, and "P" is an unvoiced sound, etc.

The speech signal can be analyzed in several ways. One useful analysis technique is spectral analysis, whereby the speech signal is analyzed in the frequency domain, and a spectrum is considered of amplitude (and phase) versus frequency. When the cavities of the speech production system are excited, a number of spectral peaks are produced, and the frequencies and relative amplitudes of these spectral peaks are also varied with time.

The number of spectral peaks ranges between about three and five and these peaks are called "formants". These formants are numbered from the lowest frequency formant, conventionally called F1, to the highest frequency formants, and the voice pitch is conventionally referred to as F0. Characteristic sounds of different vowels are produced by the speaker changing the shape of the oral and nasal cavities, which has the effect of changing the frequencies and relative intensities of these formants.

In particular, it has been found that the second formant (F2) is important for conveying vowel information. For example, the vowel sounds "oo" and "ee" may be produced with identical voicings of the vocal cords, but will sound different due to different second formant characteristics.

There is of course a variety of different sounds in speech and their method of production is complex. For the purpose of understanding the invention herein however, it is sufficient to remember that there are two main types of sounds—voiced and unvoiced; and that the time course of the frequencies and amplitudes of the formants carries most of the intelligibility of the speech signal.

The term "psychophysics" is used herein to refer to the study of the perceptions elicited in patients by electrical stimulation of the auditory nerve. For stimulation at rates between 100 and 400 pulses per second, a noise is perceived which changes pitch with stimulation rate. This is such a distinct sensation that it is possible to convey a melody to a patient by its variation.

By stimulating the electrode at a rate proportional to voice pitch (F0), it is possible to convey prosodic information to the patient. This idea is used by some cochlear implant systems as the sole method of information transmission, and may be performed with a single electrode.

It is more important to convey formant information to the patient, as this contains most of the intelligibility of the speech signal. It has been discovered by psychophysical testing that just as an auditory signal which stimulates the remote end of the cochlea produces a low frequency sensation and a signal which stimulates the near end thereof produces a high frequency sensation, a similar phenomenon will be observed with electrical stimulation. The perceptions elicited by electrical stimulation at different positions inside the cochlea have been reported by the subjects as producing percepts which vary in "sharpness" or "dullness", rather than pitch as such. However, the difference in frequency perceptions between electrodes is such that formant, or spectral peak, information can be coded by selection of electrode, or site of stimulation in the cochlea.

It has been found by psychophysical testing that the range of electrical stimulation corresponding to loudness from threshold to uncomfortably loud (typically 12 dB) is smaller than the corresponding range of acoustic signals for normally hearing people (typically 100 dB).

It has also been discovered through psychophysical testing that the pitch of sound perceptions due to electrical stimulation is also dependent upon frequency of stimulation, but the perceived pitch is not the same as the stimulation frequency. In particular, the highest pitch able to be perceived through the mechanism of the changing stimulation rate alone is in the order of 1 kHz, and stimulation at rates above this maximum level will not produce any increase in pitch of the perceived sound. In addition, for electrical stimulation within the cochlea, the perceived pitch depends upon electrode position. In multiple electrode systems, the perceptions due to stimulation at one electrode are not independent of the perceptions due to simultaneous stimulation of nearby electrodes. Also, the perceptual qualities of pitch, "sharpness", and loudness are not independently variable with stimulation rate, electrode position, and stimulation amplitude.

Some systems of cochlear implants in the prior art are arranged to stimulate a number of electrodes simultaneously in proportion to the energy in specific frequency bands, but this is done without reference to the perceptions due to stimulus current in nearby stimulating electrodes. The result is that there is interaction between the channels and the loudness is affected by this.

A number of attempts have heretofore been made to provide useful hearing through electrical stimulation of auditory nerve fibers, using electrodes inside or adjacent to some part of the cochlear structure. Systems using a single pair of electrodes are shown in U.S. Pat. No. 3,751,605 to Michelson and U.S. Pat. No. 3,752,939 to Bartz.

In each of these systems an external speech processing unit converts the acoustic input into a signal suitable for transmission through the skin to an implanted receiver/stimulator unit. These devices apply a continuously varying stimulus to the pair of electrodes, stimulating at least part of the population of auditory nerve fibers, and thus producing a hearing sensation.

The stimulus signal generated from a given acoustic input is different for each of these systems, and while some degree of effectiveness has been demonstrated for each, performance has varied widely across systems and also for each system between patients. Because the design of these systems has evolved empirically, and has not been based on detailed psychophysical observations, it has not been possible to determine the cause of this variability. Consequently, it has not been possible to reduce it.

An alternative approach has been to utilize the tonotopic organization of the cochlea to stimulate groups of nerve fibers, depending on the frequency spectrum of the acoustic signal. Systems using this technique are shown in U.S. Pat. No. 4,207,441 to Ricard, U.S. Pat. No. 3,449,768 to Doyle, U.S. Pat. No. 4,063,048 to Kissiah, and U.S. Pat. Nos. 4,284,856 and 4,357,497 to Hochmair et al.

The system described by Kissiah uses a set of analog filters to separate the acoustic signal into a number of frequency components, each having a predetermined frequency range within the audio spectrum These analog signals are converted into digital pulse signals having a pulse rate equal to the frequency of the analog signal they represent, and the digital signals are used to stimulate the portion of the auditory nerve normally carrying the information in the same frequency range. Stimulation is accomplished by placing an array of spaced electrodes inside the cochlea.

The Kissiah system utilizes electrical stimulation at rates up to the limit of normal acoustic frequency range, say 10 kHz, and independent operation of each electrode. Since the maximum rate of firing of any nerve fiber is limited by physiological mechanisms to one or two kHz, and there is little perceptual difference for electrical pulse rates above 1 kHz, it may be inappropriate to stimulate at the rates suggested. No consideration is given to the interaction between the stimulus currents generated by different electrodes, which experience shows may cause considerable uncontrolled loudness variations, depending on the relative timing of stimulus presentations. Also, this system incorporates a percutaneous connector which has with it the associated risk of infection.

The system proposed by Doyle limits the stimulation rate for any group of fibers to a rate which would allow any fiber to respond to sequential stimuli. It utilizes a plurality of transmission channels, with each channel sending a simple composite power/data signal to a bipolar pair of electrodes. Voltage source stimulation is used in a time multi-plexed fashion similar to that subsequently used by Ricard and described below, and similar uncontrolled loudness variations will occur with the suggested independent stimulation of neighboring pairs of electrodes. Further, the requirement of a number of transmission links equal to the number of electrode pairs prohibits the use of this type of system for more than a few electrodes.

The system proposed by Ricard utilizes a filter bank to analyze the acoustic signal, and a single radio link to transfer both power and data to the implanted receiver/stimulator, which presents a time-multiplexed output to sets of electrodes implanted in the cochlea. Monophasic voltage stimuli are used, with one electrode at a time being connected to a voltage source while the rest are connected to a common ground line. An attempt is made to isolate stimulus currents from one another by placing small pieces of silastic inside the scala, between electrodes. Since monophasic voltage stimuli are used, and the electrodes are returned to the common reference level after presentation of each stimulus, the capacitive nature of the electrode/electrolyte interface will cause some current to flow for a few hundred microseconds after the driving voltage has been returned to zero. This will reduce the net transfer of charge (and thus electrode corrosion) but this charge recovery phase is now temporarily overlapped with the following stimulus or stimuli. Any spatial overlap of these stimuli would then cause uncontrolled loudness variations.

In the Hochmair et al. patents a plurality of carrier signals are modulated by pulses corresponding to signals in audio frequency bands. The carrier signals are transmitted to a receiver having independent channels for receiving and demodulating the transmitted signals. The detected pulses are applied to electrodes on a cochlear implant, with the electrodes selectively positioned in the cochlea to stimulate regions having a desired frequency response. The pulses have a frequency which corresponds to the frequency of signals in an audio band and a pulse width which corresponds to the amplitude of signals in the audio band.

U.S. Pat. No. 4,267,410 to Forster et al. describes a system which utilizes biphasic current stimuli of predetermined duration, providing a good temporal control of both stimulating and recovery phases. However, the use of fixed pulse duration prohibits variation of this parameter which may be required by physiological variations between patients. Further, the data transmission system described in this system severely limits the number of pulse rates available for constant rate stimulation.

U.S. Pat. No. 4,593,696 to Hochmair et al. describes a system in which at least one analog electrical signal is applied to implanted electrodes in a patient, and at least one pulsatile signal is applied to implanted electrodes. The analog signal represents a speech signal, and the pulsatile signal provides specific speech features such as formant frequency and pitch frequency.

U.S. Pat. No. 4,515,158 to Patrick et al. describes a system in which sets of electrical currents are applied to selected electrodes in an implanted electrode array. An incoming speech signal is processed to generate an electrical input corresponding to the received speech signal, and electrical signals characterizing acoustic features of the speech signal are generated from the input signal. Programmable means obtains and stores data from the electrical signals and establishes sets of electric stimuli to be applied to the electrode array, and instruction signals are produced for controlling the sequential application of pulse stimuli to the electrodes at a rate derived from the voicing frequency of the speech signal for voiced utterances and at an independent rate for unvoiced utterances.

The state of the art over which the present invention represents an improvement is perhaps best exemplified by the aforesaid U.S. Pat. No. 4,532,930 to Crosby et al., entitled "Cochlear Implant System for an Auditory Prosthesis". The subject matter of said Crosby et al. patent is hereby incorporated herein by reference. The Crosby et al. patent describes a cochlear implant system in which an electrode array comprising multiple platinum ring electrodes in a silastic carrier is implanted in the cochlea of the ear. The electrode array is connected to a multichannel receiver-stimulating unit, containing a semiconductor integrated circuit and other components, which is implanted in the patient adjacent the ear. The receiver-stimulator unit receives data information and power through a tuned coil via an inductive link with a patient-wearable external speech processor. The speech processor includes an integrated circuit and various components which are configured or mapped to emit data signals from an Erasable Programmable Read Only Memory (EPROM). The EPROM is programmed to suit each patient's electrical stimulation perceptions, which are determined through testing of the patient and his implanted stimulator/electrode. The testing is performed using a diagnostic and programming unit (DPU) that is connected to the speech processor by an interface unit.

The Crosby et al. system allows use of various speech processing strategies, including dominant spectral peak and voice pitch, so as to include voiced sounds, unvoiced glottal sounds and prosodic information. The speech processing strategy employed is based on known psychophysical phenomena, and is customized to each individual patient by the use of the diagnostic and programming unit. Biphasic pulses are supplied to various combinations of the electrodes by a switch controlled current sink in various modes of operation. Transmission of data is by a series of discrete data bursts which represent the chosen electrode(s), the electrode mode configuration, the stimulating current, and biphasic pulse duration.

Each patient will have different perceptions resulting from electrical stimulation of the cochlea. In particular, the strength of stimulation required to elicit auditory perceptions of the same loudness may be different from patient to patient, and from electrode to electrode for the same patient. Patients also may differ in their abilities to perceive pitch changes from electrode to electrode.

The speech processor accommodates differences in psychophysical perceptions between patients and compensates for the differences between electrodes in the same patient. Taking into account each individual's psychophysical responses, the speech processor encodes acoustic information with respect to stimulation levels, electrode frequency boundaries, and other parameters that will evoke appropriate auditory perceptions. The psychophysical information used to determine such stimulation parameters from acoustic signals is referred to as a MAP and is stored in a random access memory (RAM) inside the speech processor. An audiologist generates and "fine tunes" each patient's MAP using a diagnostic and programming system (DPS). The DPS is used to administer appropriate tests, present controlled stimuli, and confirm and record test results.

The multi-electrode cochlear prosthesis has been used successfully by profoundly deaf patients for a number of years and is a part of everyday life for many people in various countries around the world. The implanted part of the prosthesis has remained relatively unchanged except for design changes, such as those made to reduce the overall thickness of the device and to incorporate an implanted magnet to eliminate the need for wire headsets.

The external speech processor has undergone significant changes since early versions of the prosthesis. The speech coding scheme used by early patients presented three acoustic features of speech to implant users. These were amplitude, presented as current level of electrical stimulation; fundamental frequency or voice pitch, presented as rate of pulsatile stimulation; and the second formant frequency, represented by the position of the stimulating electrode pair. This coding scheme (F0F2) provided enough information for profoundly postlinguistically deafened adults to show substantial improvements in their perception of speech.

The early coding scheme progressed naturally to a later coding scheme in which additional spectral information is presented. In this scheme a second stimulating electrode pair was added, representing the first formant of speech. The new scheme (F0F1F2) showed improved performance for adult patients in all areas of speech perception.

Despite success of speech processors using the F0F1F2 scheme over the last few years, a number of who perform well in quiet conditions can have significant problems when there is a moderate level of background noise. Also, the F0F1F2 scheme codes frequencies up to about 3500 Hz; however, many phonemes and environmental sounds have a high proportion of their energy above this range making them inaudible to the implant user in some cases.

It is, therefore, a primary object of the present invention to provide an improved cochlear implant system which overcomes various of the problems associated with earlier cochlear implant systems.

Another object of the invention is to provide, in a cochlear implant system, an improved speech coding scheme in which all of the information available in earlier coding schemes is retained and additional information from additional high frequency band pass filters is provided.

Further objects or advantages of this invention will become apparent as the following description proceeds.

DISCLOSURE OF THE INVENTION

Briefly stated and in accordance with one embodiment of this invention, there is provided an improved pulsatile system for a cochlear prosthesis in which an incoming audio signal is concurrently presented to a speech feature extractor and a plurality of band pass filters, the pass bands of which are different from one another and at least one of which is at a higher frequency than the normal range of the second formant or frequency peak of the speech signal. The energy within these pass bands controls the amplitude of electrical stimulation of a corresponding number of fixed electrode pairs adjacent the basal end of the electrode array, thus providing additional information about high frequency sounds at a tonotopically appropriate place within the cochlea. Preferably three additional band pass filters are employed in the ranges of 2000-2800 Hz, 2800-4000 Hz and 4000-8000 Hz.

The overall stimulation rate remains as F0 (fundamental frequency or voice pitch) but, in addition, four electrical stimulation pulses occur for each glottal pulse, as compared with the F0F1F2 strategy heretofore used, in which only two pulses occur per voice pitch period. For voiced speech sounds, pulses representing the first and second formant are provided along with additional stimulation pulses representing energy in the 2000-2800 Hz and the 2800-4000 Hz ranges. For unvoiced phonemes, yet another pulse representing energy above 4000 Hz is provided while no stimulation for the first formant is provided, since there is no energy in this frequency range. Stimulation occurs at a random pulse rate of approximately 260 Hz, which is about double that used in earlier speech coding schemes.

More particularly, and in accordance with another aspect of the present invention, an improved speech processor for a cochlear prosthesis is provided. The speech processor employs a multi-spectral peak (MPEAK) coding strategy to extract a number, for example five, of spectral peaks from an incoming acoustic signal received by a microphone. The speech processor encodes this information into sequential pulses that are sent to selected electrodes of a cochlear implant. The first formant (F1) spectral peak (280-1000 Hz) and the second formant (F2) spectral peak (800-4000 Hz) are encoded and presented to apical and basal electrodes, respectively. F1 and F2 electrode selection follows the tonotopic organization of the cochlea. High-frequency spectral information is sent to more basal electrodes and low-frequency spectral information is sent to more apical electrodes. Spectral energy in the regions of 2000-2800 Hz, 2800-4000 Hz, and above 4000 Hz is encoded and presented to three fixed electrodes. The fundamental or voicing frequency (F0) determines the pulse rate of the stimulation during voiced periods and a pseudo-random aperiodic rate determines the pulse rate of stimulation during unvoiced periods. The amplitude of the acoustic signal in the five bands determines the stimulus intensity.

BRIEF DESCRIPTION OF THE DRAWINGS

While the specification concludes with claims particularly pointing out and distinctly claiming the subject matter of this invention, it is believed that the invention will be better understood from the following description, taken in conjunction with the accompanying drawing, in which:

FIG. 2 is a block diagram of the overall cochlear implant system of this invention;

FIG. 3 is a pictorial view of the components of this system, including the implantable parts and the parts worn by the patient;

BEST MODE FOR CARRYING OUT THE INVENTION

Figure 1A:
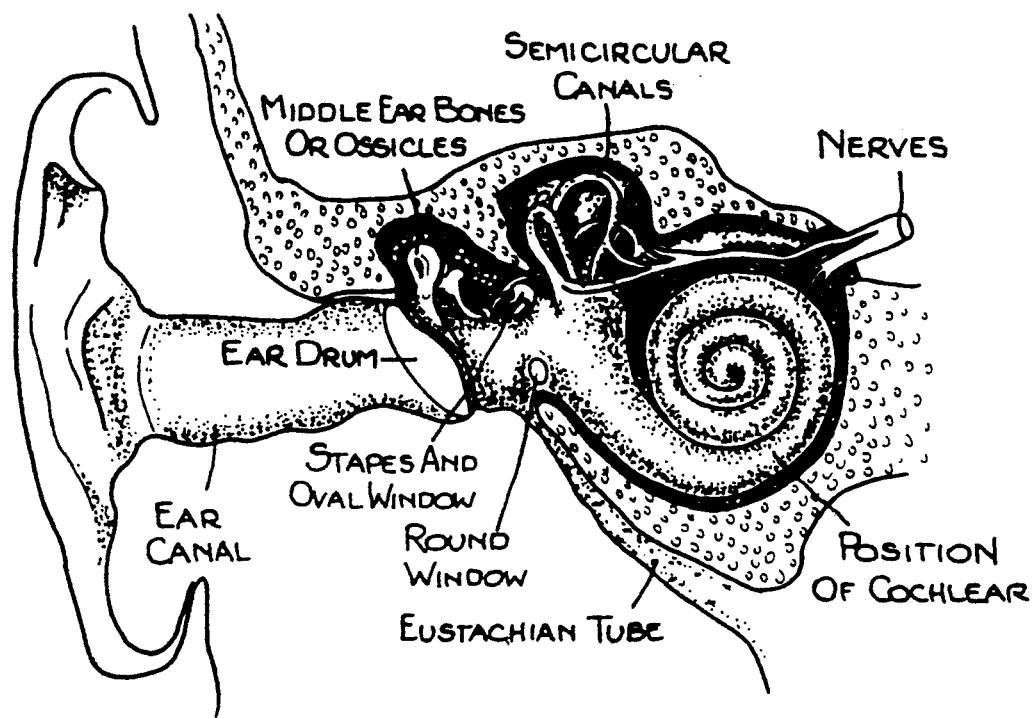
FIGS. 1A and 1B are interior views of the anatomy of a human ear and a cross section of a cochlea, respectively.

The cochlear implant system of this invention, shown in FIG. 2, comprises several components. An electrode array 1 is implanted into the cochlea. The electrode array 1 comprises a number of rings or bands of platinum molded with a flexible silastic carrier. Preferably, there are 32 bands of platinum in total. The distal 22 bands are active electrodes, and have connecting wires welded to them. The proximal 10 electrode bands are used for stiffening, and to act as an aid to surgical insertion. In a typical array, the electrode rings are about 0.05 mm in thickness with a width of 0.3 mm, and have outside diameters ranging from 0.6 mm at the proximal end to 0.4 mm diameter at the distal end. The diameter of the rings changes smoothly so that the array is tapered over the distal 10 mm or so. The rings are spaced on 0.75 mm centers over the distal 25 mm of the electrode array, and all of the exposed outside area of the rings is used as active electrode area. The silastic material may be MDX4-4210, manufactured by Dow Corning.

The 22 electrode wires pass via a cable 2 from the electrode array 1 to the receiver-stimulator unit (RSU) 3. The invention described is not limited to the use of this design of electrode array, and a number of alternative electrode designs as have been described in the prior art could be used. The RSU 3 receives information and power from an external source through a tuned receiving coil 5 attached to the RSU and positioned just beneath the skin. The RSU also provides electrical stimulating pulses to the electrode array 1. The power, and data on which electrode to stimulate, and with what intensity, is transmitted across the skin using an inductive link 6 operating at radio frequencies, from an external multipeak speech processor (MSP) 7. In normal operation, the MSP picks up acoustic stimuli from a microphone 8 conveniently worn, and extracts from the signal, information which is used to determine stimulation electrode, rate and amplitude.

Because each patient's response to electrical stimulation is different, it is necessary to configure each patient's MSP to his or her own requirements. Thus, the MSP has a random access memory (RAM) which is programmed to suit each patient.

The patient's response to electrical stimulation is tested some short time after implantation of the RSU 3, using the patient's MSP, and the results of these tests are used to set up the MSP for the patient's own particular requirements. This is done by connecting the MSP, via a connector and cables 9, to a diagnostic programming interface unit (DPI) 10. The DPI is itself connected via a cable and connector 11 to a general purpose computer referred to as a diagnostic and programming unit (DPU) 12

Figure 1B:
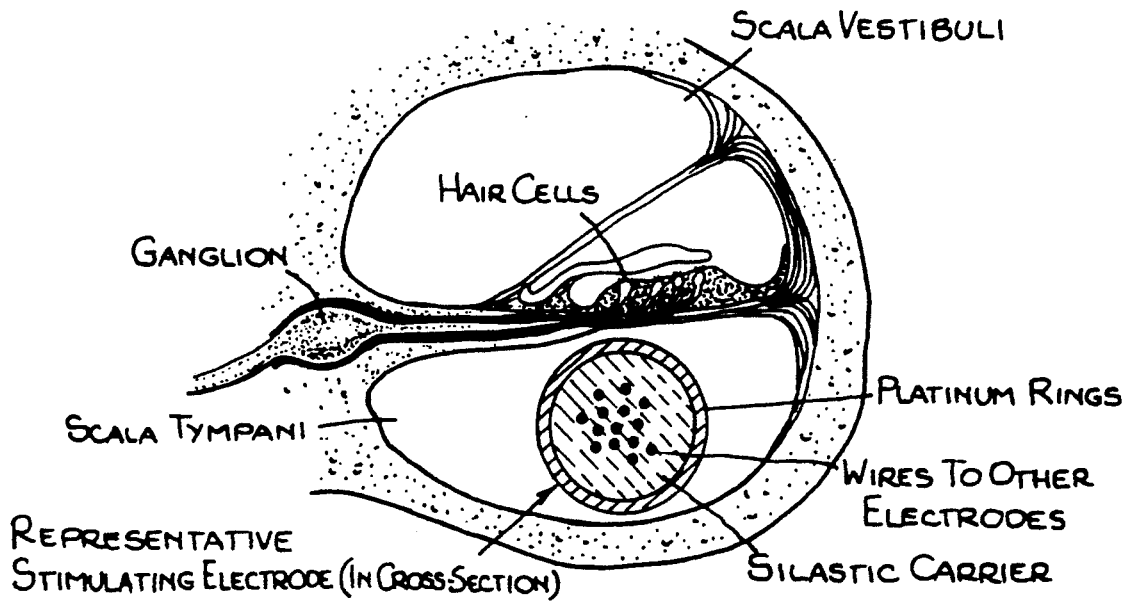
Figure 3A:
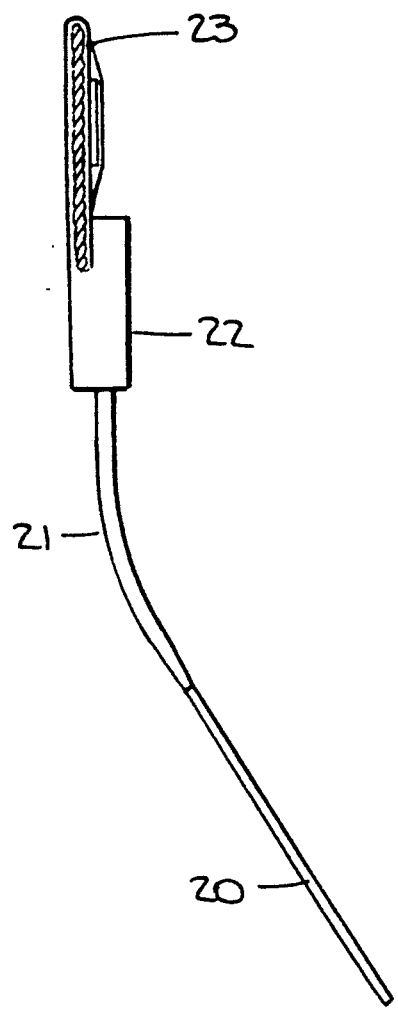
FIGS. 3A and 3B are respective side and end elevation views of the implantable parts of this system.
Figure 3B:
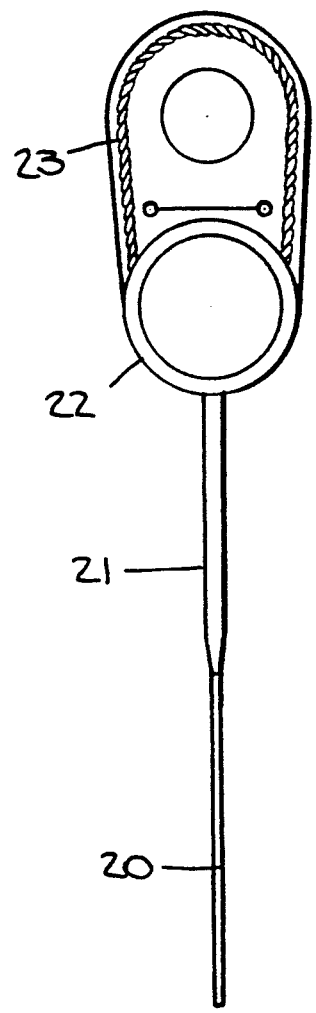

A pictorial representation of the system used by the patient is shown in FIGS. 3, 3A and 3B. The electrode array 20 is flexible and fits the shape of the cochlea (FIGS. 1A and 1B) as it is inserted along the basilar membrane separating the scala tympani from the remainder of the cochlea. The electrode array is connected via a silastic-covered cable 21 to the RSU 22. Cable 21 is specially designed to provide stress relief to prevent fracture of the wire in the cable. The receiving coil for information and power is a single turn of multistrand platinum wire 23 which is transformer coupled to the implanted electronics in the RSU 22.

An externally worn transmitting coil 24 is held against the head over the site of the RSU implant 22 by, cooperating magnets (not shown) carried adjacent each of the coils 23 and 24. Coil 24 is connected to the speech processor 29 via a coil cable 26 and a hearing aid microphone 27. Hearing aid microphone 27 is worn on the ear nearest to the implant site and audio data from the microphone 27 is connected via a three wire cable 28 to the MSP 29. Transmission data is connected to the coil 24 from the MSP 29 via the same three wire cable 28 and via the coil cable 26. This three wire arrangement is described in the copending U.S. patent application Ser. No. 404,230, filed Sep. 7, 1989, of Christopher N. Daly, entitled "Three Wire System For Cochlear Implant Processor," which application is assigned to the assignee of the present invention and is incorporated herein by reference. Alternative microphone configurations are possible, including a microphone worn on a tie clasp or attached to the user's clothing, or the like.

The coil cable 26 and three wire cable 28 are attached to the microphone 27 and MSP 29 by demountable connectors 32, 33 and 34. The MSP 29 is powered by conventionally available batteries (e.g., a single AA size cell) carried inside the MSP 29. A plug-in jack 31 is provided to allow connection of external audio signal sources, such as from a television, radio, or high quality microphone.

Figure 4:
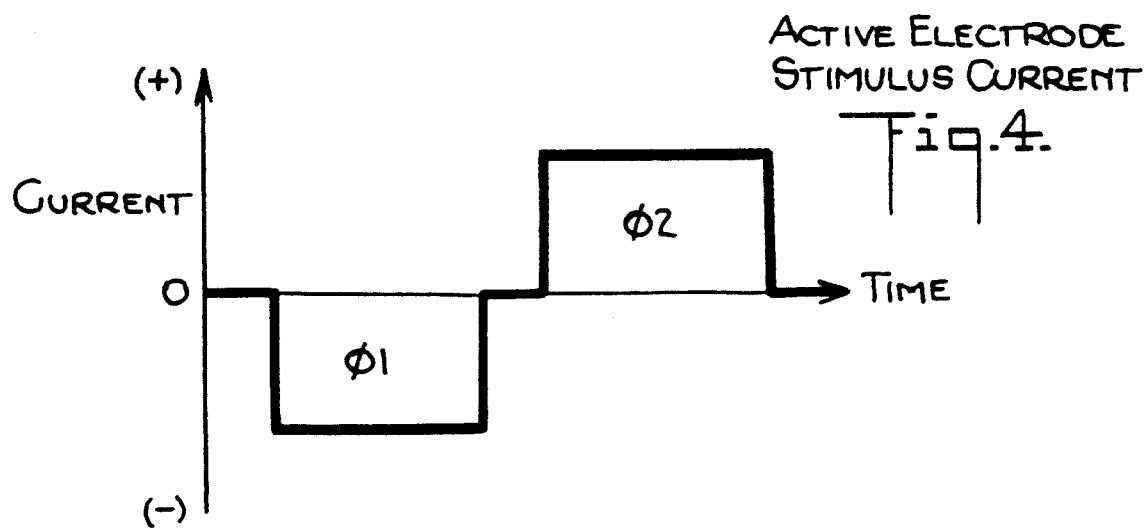
FIG. 4 is a graph of current vs. time, showing the biphasic current waveform utilized in this invention.

Referring to FIG. 4, the pulse which is used to electrically stimulate the cochlea is biphasic. That is, it comprises a period of negative current stimulation, followed by an equal period of positive current stimulation of equal amplitude, the two periods (known as phases phi 1 and phi 2), separated by a short period of no stimulation. Phi 1 and phi 2 may be in the range of 12 to 400 microseconds (typically 200 microseconds), and the intervening interval is typically about 50 microseconds. The amplitudes of phi 1 and phi 2, their durations, and the duration of the intervening interval are determined by the information decoded from the signal transmitted by the speech processor 29 (FIG. 3). The actual values of these parameters will be set up on an electrode by electrode basis, for each patient, as a result of psychophysical testing of the patient. The reversal in polarity of phi 1 and phi 2 is important since it ensures that there is no net DC component in the stimulus. This is important because long term DC excitation might cause electrode corrosion, and possible subsequent damage to the cochlea itself The questions of electrode electrochemistry and charge balance are thought to be more important in cochlear implants than in, say, cardiac pacemakers which are well known in the art. This is because a cochlear stimulator will be stimulating nerve fibers, whereas a cardiac pacemaker is designed to stimulate cardiac muscle. It is thought that nerve tissues may be more susceptible to damage due to electrical stimulation, and thus the cochlear implant system is designed with more stringent safety factors than cardiac pacemakers. The system is designed so that the same stimulus source is used for both stimulation phases. The biphasic pulse is produced simply by reversal of the connections to the electrodes. Thus, extremely good charge symmetry is obtained, resulting in a high level of safety, provided the durations of phi 1 and phi 2 are equal.

The stimulation circuitry is preferably configured as a constant current source. This has the advantage compared to a constant voltage source that if the electrode impedance changes (as has often been observed) the delivered current to the electrode will remain unaltered over a large range of electrode impedances. The current may be varied from a few microamps to 2 mA, allowing a very large range of loudness percepts to be produced and large variations between patients to be accommodated.

The stimulus generation circuitry in the RSU 3 (FIG. 2) is preferably designed to operate in one of two modes. The first mode is referred to as "multipolar" or "common ground" stimulation. In this mode, one electrode is selected to be the "active" electrode, and all other electrodes operate as a common current source. In phase phi 2, the connections are reversed so that the "active" electrode acts as the current source and the common electrodes act as a current sink. The choice of stimulus order is not determined by any limitations or restrictions in the circuit design, and either way may be chosen when implementing the circuit design.

The second mode is "bipolar" stimulation. In this mode stimulation is between two selected electrodes, let us say A and B. In phase phi 1, current is sourced by A, and sunk by B. In phase phi 2, current is sourced by B, and sunk by A, and no other electrodes play any part in stimulation. The RSU 3 is preferably configured so that any pair of electrodes may be selected for bipolar stimulation. Thus there is great flexibility in choice of stimulation strategy.

It should be understood that only these two particular stimulation modes have been chosen. Other stimulation modes are not excluded, however. For example, a multipolar or distributed ground system could be used where not all other electrodes act as a distributed ground, and any electrode could be selected at any time to be a current source, current sink, or inactive during either stimulation phase with suitable modification of the receiver-stimulator.

The main aim of this invention is to provide improved speech communication to those people suffering from profound hearing loss. However, in addition to providing improved speech communication, it is also important to be able to convey environmental sounds, for example telephones, doors, warning sirens, door bells, etc., which form part of a person's life. The system described up to now is basically that of the Crosby et al. patent, heretofore referred to and incorporated herein by reference. In the Crosby et al. patent it is recognized that the second formant F2 carries most of the intelligibility of the speech signal, while the first formant F1, although containing much of the naturalness of the signal, contributes less to intelligibility.

Crosby et al. observed that the third and higher formants do not carry as much information as the second formant They also felt that in view of the then limitations of knowledge on the interaction between electrodes when a number of electrodes are stimulated simultaneously, the most effective method of stimulation would be to code the second formant on an appropriate electrode or site in the cochlea to provide the most important formant information. The amplitude of such stimulation is derived from the amplitude of the second formant.

The Crosby et al. system also provides prosodic information in the form of pulse rate. That system compresses the stimulation rate to the range 100-250 Hz.

An additional factor employed in Crosby et al. is that only the top 10 to 20 dB of current acoustic stimulus level is used to determine stimulus amplitude. That is, instead of compressing the entire acoustic loudness range into the small range of electrical stimulation available, only the top part is used. Thus, Crosby et al.'s amplitude of the signal is entirely represented by a five bit binary code, which provides only 30 dB of dynamic range.

In summary, the Crosby et al. speech processing strategy is:
1. The dominant spectral peak in the range of about 900 Hz to about 4000 Hz is used to encode electrode position.
2. The amplitude of the dominant spectral peak used to encode electrode position is used to determine stimulation amplitude.
3. Voice pitch (F0) is compressed and used to determine the stimulation rate.

For unvoiced sounds and, environmental sounds, the Crosby et al. system still generates stimuli, but the stimulation rate and electrode position will be determined by the exact nature of the acoustic signal. For example, for sibilant consonants ("s"), the stimulation rate is fairly fast, but not constant, and the electrode stimulated will be one which illicits a high frequency percept.

A second speech processing strategy, useful in some patients, is employed in Crosby et al. The second strategy is similar to the one mentioned above in that electrode position is encoded from formant frequency. However, the stimulation rate is at the F1 or first formant frequency, and the stimulation amplitude is determined for the value of the peak of the acoustic signal at the time of the F1 peak. This has the advantage that the stimulation rate is faster, and elicits more natural sounding speech perceptions in some patients. In addition, since the F1 signal is amplitude modulated and temporally better than the F0 rate, the patients also perceive the F0 or voice pitch which is useful for conveying prosodic information.

Another speech processing strategy considered in the Crosby et al. reference is to stimulate the patient at the rate of F1 extracted from an incoming speech signal, but to pattern the stimulation such that the stimuli are gated at the F0 rate.

Notwithstanding the success of speech processors using the Crosby et al. F0, F1, F2 speech processing coding scheme over the last few years, a number of problems still remain in connection with the use of such speech processor coding schemes. As indicated earlier, patients who perform well in quiet conditions can have significant problems when there is a moderate level of background noise. Moreover, since the F0,F1,F2 scheme codes frequencies up to about 4000 Hz, and many phonemes and environmental sounds have a high proportion of their energy above this range, such phonemes and environmental sounds are inaudible to the implant user in some cases.

In accordance with the present invention multichannel cochlear implant prostheses having a pulsatile operating system, such as that disclosed in the Crosby et al. reference, are provided with a speech coding scheme in which the speech signal is bandpass filtered into a number of bands, for example 3, within and beyond the normal range of the second frequency peak or formant F2 of the speech signal. The speech coding scheme disclosed herein is referred to as the multi-spectral peak coding strategy (MPEAK). MPEAK is designed to provide additional high-frequency information to aid in the perception of speech and environmental sounds.

The MPEAK coding strategy extracts and codes the F1 and F2 spectral peaks, using the extracted frequency estimates to select a more apical and a more basal pair of electrodes for stimulation. Each selected electrode is stimulated at a pulse rate equal to the fundamental frequency F0. In addition to F1 and F2, three high frequency bands of spectral information are extracted. The amplitude estimates from band three (2000–2800 Hz), band four (2800–4000 Hz), and band five (above 4000 Hz) are presented to fixed electrodes, for example the seventh, fourth and first electrodes, respectively, of the electrode array 1 (FIG. 2).

The first, fourth and seventh electrodes are selected as the default electrodes for the high-frequency bands because they are spaced far enough apart so that most patients will be able to discriminate between stimulation at these three locations. Note that these default assignments may be reprogrammed as required. If the three high frequency bands were assigned only to the three most basal electrodes in the MAP, many patients might not find the additional high frequency information as useful since patients often do not demonstrate good place-pitch discrimination between adjacent basal electrodes. Additionally, the overall pitch percept resulting from the electrical stimulation might be too high.

Table I below indicates the frequency ranges of the various formants employed in the speech coding scheme of the present invention.

TABLE I

| Frequency Range | Formant or Band |
|---|---|
| 280–1000 Hz | F1 |
| 800–4000 Hz | F2 |
| 2000–2800 Hz | Band 3 - Electrode 7 |
| 2800–4000 Hz | Band 4 - Electrode 4 |
| 4000 Hz and above | Band 5 - Electrode 1 |

Figure 5:
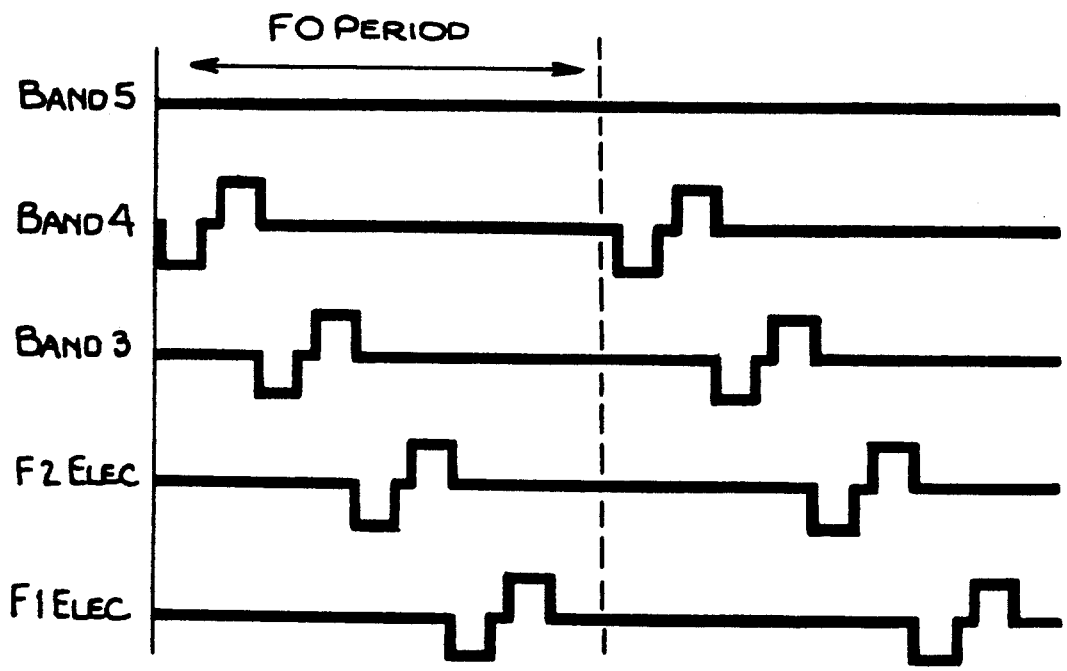
FIG. 5 is a graph showing an example of the sequential stimulation pattern of electrode pairs for a voiced sound using the multi-peak coding strategy of this invention.

If the input signal is voiced, it has a fundamental frequency. The electrode pairs selected from the estimates of F1, F2 and bands 3 and 4 are stimulated sequentially at the rate equal to F0. The most basal electrode pair is stimulated first, followed by progressively more apical electrode pairs, as shown in FIG. 5. Band 5 is not presented in FIG. 5 because negligible information is contained in this frequency band for voiced sounds.

Figure 6:
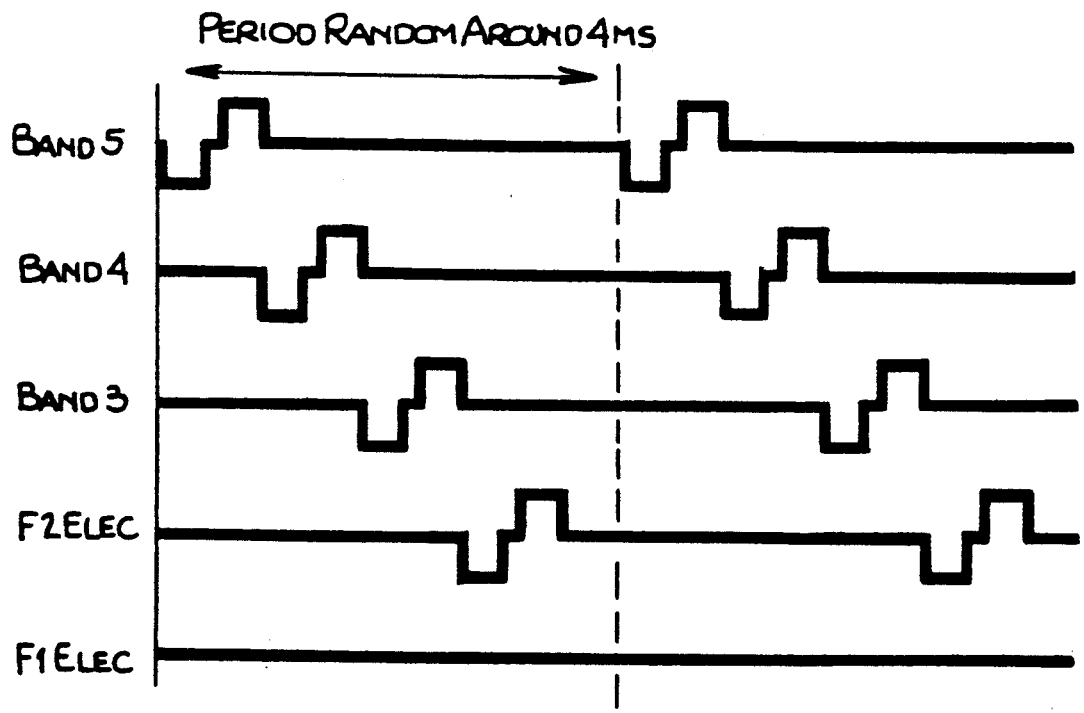
FIG. 6 is a graph showing an example of the sequential stimulation pattern of electrode pairs for an unvoiced sound using the multi-peak coding strategy of this invention.
Figure 7:
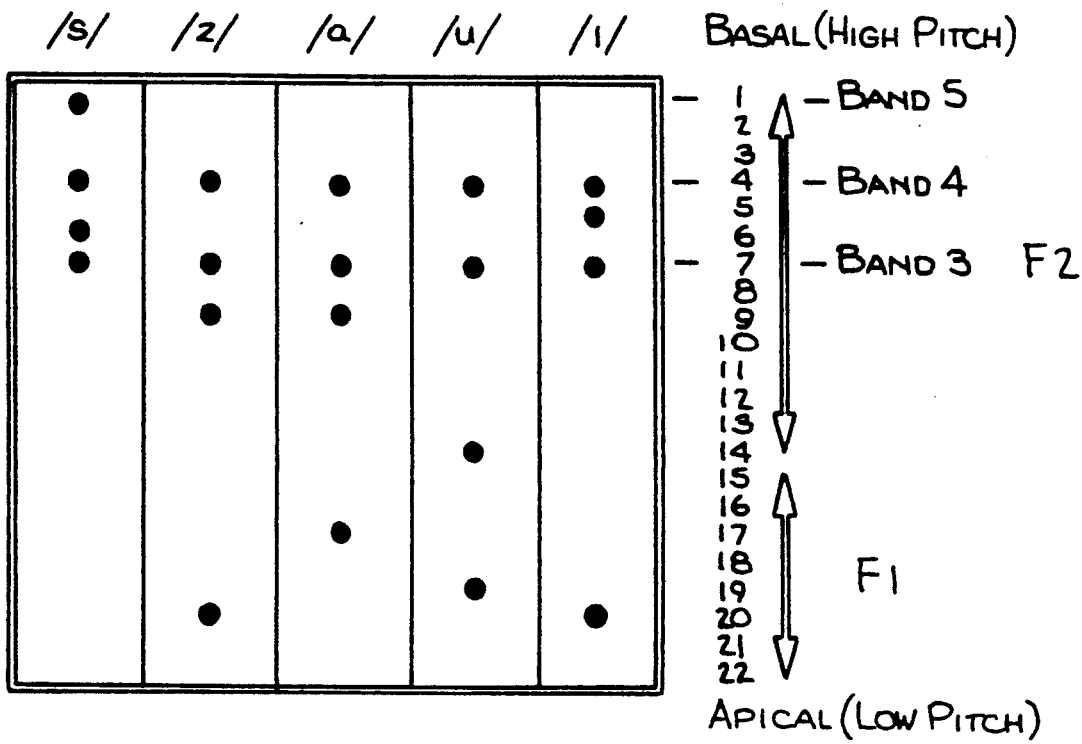
FIG. 7 is a chart showing an example of the pattern of electrical stimulation for various steady-state phonemes using the multi-peak coding strategy of this invention.

If the input signal is unvoiced, energy in the F1 band (280–1000 Hz) is typically smaller than energy in higher frequency bands. Consequently it is replaced with the frequency band that extracts information above 4000 Hz. In this situation, the electrode pairs selected from the estimates of F2, and bands 3, 4 and 5 receive the pulsatile stimulation. The rate of stimulation is aperiodic and varies between 200–300 Hz. FIG. 6 shows the sequential stimulation pattern for an unvoiced sound, with stimulation progressing from base to apex. The MPEAK coding strategy thus may be seen to extract and code five spectral peaks but only four spectral peaks are encoded for any one stimulus sequence FIG. 7 illustrates the pattern of electrical stimulation for various steady state phonemes when using the MPEAK coding strategy. A primary function of the MAP is to translate the frequency of the dominant spectral peaks (F1 and F2) to electrode selection. To perform this function, the electrodes are numbered sequentially starting at the round window of the cochlea. Electrode 1 is the most basal electrode and electrode 22 is the most apical in the electrode array. Stimulation of different electrodes normally results in pitch perceptions that reflect the tonotopic organization of the cochlea. Electrode 22 elicits the lowest place-pitch percept, or the "dullest" sound. Electrode 1 elicits the highest place-pitch percept, or "sharpest" sound.

To allocate the frequency range for the F1 and F2 spectral peaks to the total number of electrodes, a default mapping algorithm splits up the total number of electrodes available to use into a ratio of approximately 1:2, as shown in FIG. 7. Consequently, approximately one-third of the electrodes are assigned to the F1 frequency range. These are the more apical electrodes and they will cover the frequency range of 280–1000 Hz. The remaining two-thirds of the electrodes are assigned to the F2 frequency range (800–4000 Hz). The most apical electrodes, which cover the frequency range from 280–1000 Hz, are assigned linearly equal frequency bands. The frequency range corresponding to the estimate of F2 is assigned to the remaining more basal electrodes and is divided into logarithmically equal frequency bands. This frequency distribution is called linear/log (lin/log) spacing.

A second optional mapping algorithm (not shown) splits up the total frequency range into logarythmically equal frequency bands for both F1 and F2 electrode groups (log/log spacing). In comparison to the lin/log spacing, this results in relatively broad frequency bands for electrodes that are assigned frequency boundaries below 1000 Hz. Because of the wider frequency bands for these electrodes, many vowel sounds will stimulate similar electrodes, thus making discrimination of these vowels difficult.

The F1/F2 lin/log function of the default algorithm is preferable because it gives better spatial resolution in the F1 range than the log/log function. In addition, this algorithm provides discrimination of vowels and consonants with formants close to 1000 Hz.

The mapping section of the DPS program allows flexibility in assigning frequency bands to electrodes. If fewer electrodes are included in the MAP, then fewer and wider frequency bands are allocated automatically by the computer so that the entire frequency range is covered. Furthermore, it is possible to override the computer-generated spacing of frequency bands. Any range of frequencies may be allocated to any electrode or electrodes by changing the upper frequency boundaries.

Table II, below, shows the default boundaries (lin/log) for a MAP created in the biphasic +1 mode using 20 electrode pairs and the MPEAK coding strategy.

TABLE II

Lin/Log Frequency Boundaries for 20 Electrodes in a BP +1 Mode. Also Shown are the electrode allocations for the three high frequency bands.

| Electrode | Frequency Boundaries | |
|---|---|---|
| | Lower | Upper |
| 20 | 280 | 400 |
| 19 | 400 | 500 |
| 18 | 500 | 600 |
| 17 | 600 | 700 |
| 16 | 700 | 800 |
| 15 | 800 | 900 |
| 14 | 900 | 1000 |
| 13 | 1000 | 1112 |
| 12 | 1112 | 1237 |
| 11 | 1237 | 1377 |
| 10 | 1377 | 1531 |
| 9 | 1531 | 1704 |
| 8 | 1704 | 1896 |
| 7 | 1896 | 2109 |
| 6 | 2109 | 2346 |
| 5 | 2346 | 2611 |
| 4 | 2611 | 2904 |
| 3 | 2904 | 3231 |
| 2 | 3231 | 3595 |
| 1 | 3595 & above | |
| Electrodes: for Band 3 - 7 | | |
| for Band 4 - 4 | | |
| for Band 5 - 1 | | |

Table III, below, shows the default boundaries in the same mode using only 14 electrode pairs and the MPEAK coding strategy.

TABLE III

Lin/Log Frequency Boundaries for 14 Electrodes in a BP +1 Mode. Also shown are the electrode allocations for the three high frequency bands.

| Electrode | Frequency Boundaries | |
|---|---|---|
| | Lower | Upper |
| 20 | 280 | 400 |
| 18 | 400 | 550 |
| 17 | 550 | 700 |
| 16 | 700 | 850 |
| 15 | 850 | 1000 |
| 14 | 1000 | 1166 |
| 13 | 1166 | 1360 |
| 10 | 1360 | 1587 |
| 9 | 1587 | 1851 |
| 8 | 1851 | 2160 |

TABLE III-continued

Lin/Log Frequency Boundaries for 14 Electrodes in a BP +1 Mode. Also shown are the electrode allocations for the three high frequency bands.

| Electrode | Frequency Boundaries | |
|---|---|---|
| | Lower | Upper |
| 7 | 2160 | 2519 |
| 6 | 2519 | 2939 |
| 5 | 2939 | 3428 |
| 4 | 3428 & above | |
| Electrodes: for Band 3 - 8 | | |
| for Band 4 - 6 | | |
| for Band 5 - 4 | | |

The amplitude of the electrical stimulus is determined from the amplitude of the incoming acoustic signal within each of the five frequency bands (F1, F2, Bands 3, 4 and 5). However, because the electrodes have different threshold (T) and maximum acceptable loudness (C) levels, the speech processor must determine the level of stimulation for each electrode separately based on the amplitude of the incoming signal in each band.

Figure 8:
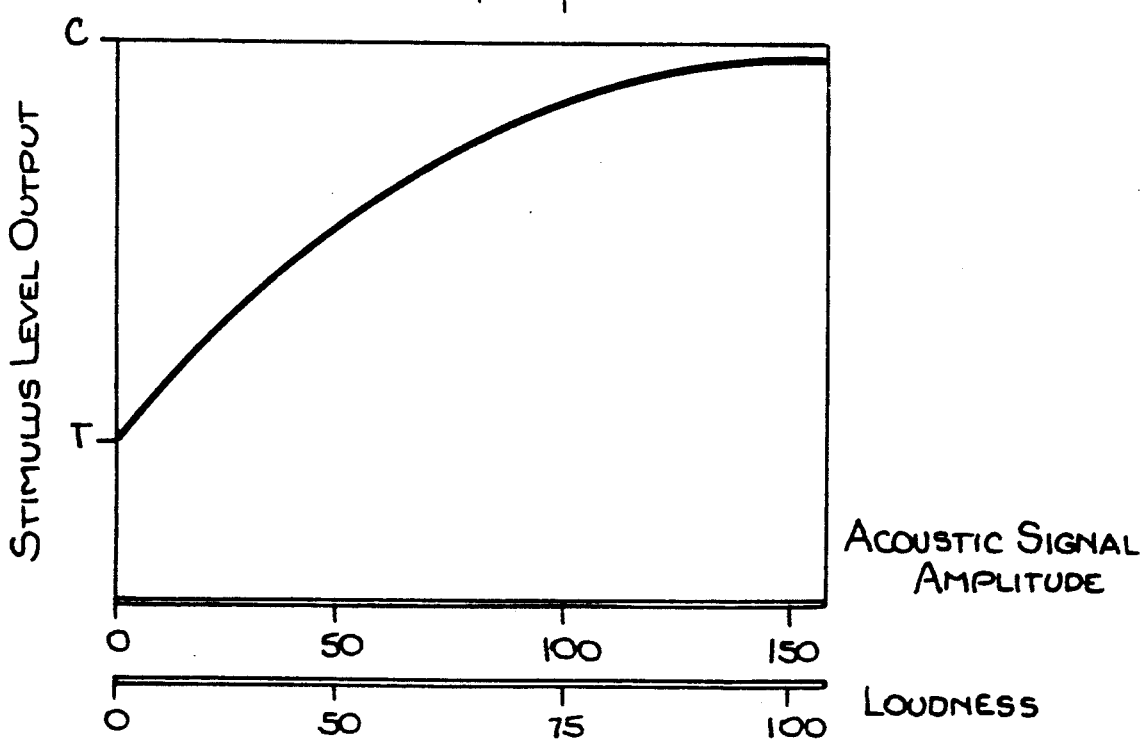
FIG. 8 is a graph showing the standard loudness growth function for the speech processor of this invention; and, FIG. 9 is a block diagram of the microphone and speech processor portions of a pulsatile type, multichannel cochlear implant system in accordance with this invention.

The MSP (FIG. 2) contains a non-linear loudness growth algorithm that converts acoustic signal amplitude to electrical stimulation parameters. First, the MSP converts the amplitude of the acoustic signal into a digital linear scale with values from 0 to 1–50, as may be seen now by reference to FIG. 8. That digital scale (in combination with the T and C-levels stored in the patient's MAP) determines the actual charge delivered to the electrodes. Signals whose amplitude levels are coded as 1 will cause stimulation at the T-level. Signals whose amplitude levels are coded as 150 will cause stimulation at the C-level.

Figure 9:
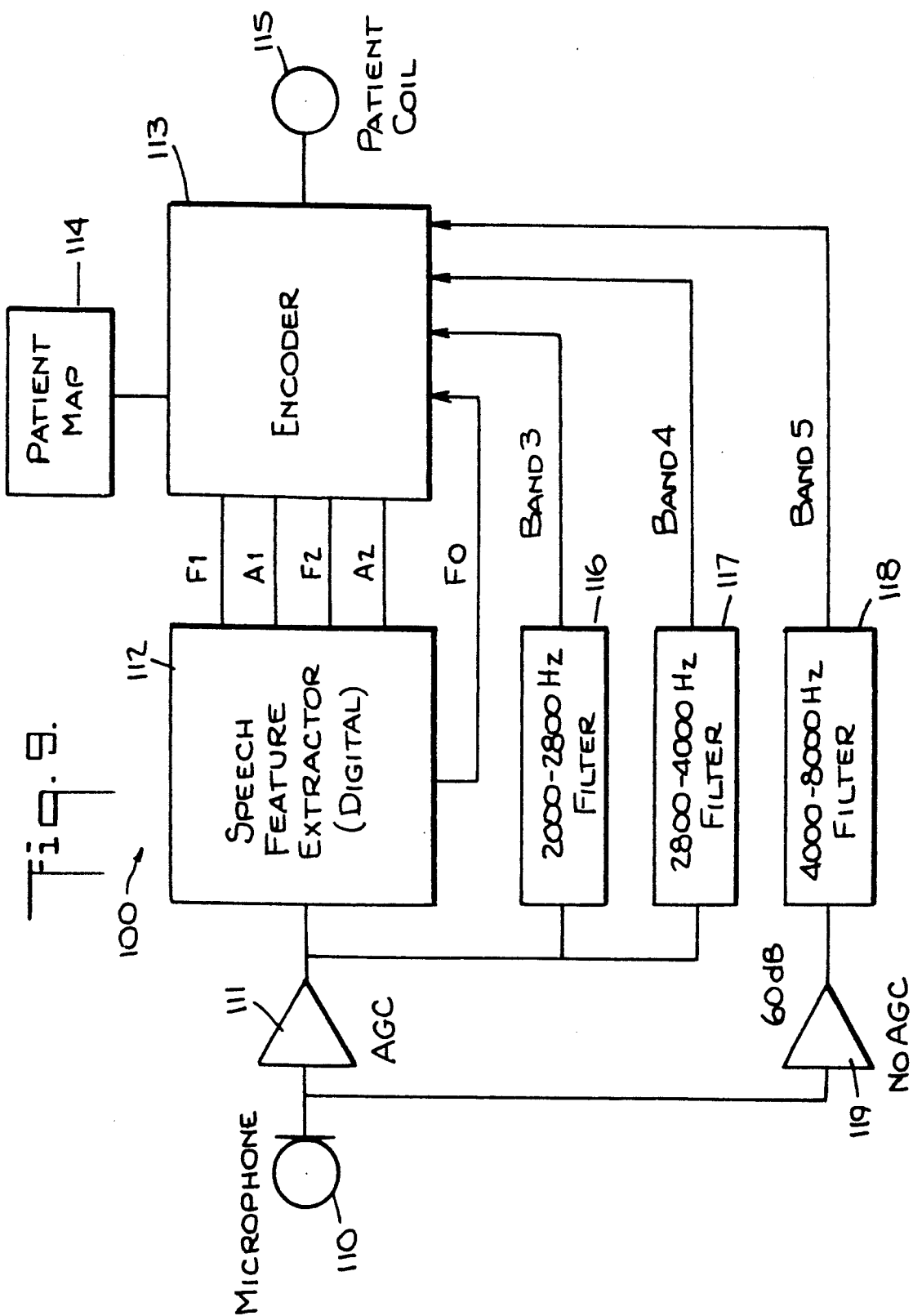

Referring now to FIG. 9, a block diagram of the microphone and speech processor portions of a pulsatile type, multi-channel cochlear implant system 100 have there been illustrated. The system 100 includes a microphone 110 which picks up speech and provides electrical audio signals to a speech feature extractor 112 through an automatic gain control amplifier 111. The speech feature extractor 112 analyzes the signals and provides digital outputs corresponding to the frequencies and amplitudes of the first and second formants, identified as F1, A1, F2 and A2, respectively, in FIG. 10.

The speech feature extractor 112 also detects and outputs the voice pitch F0 and starts the encoder 113, which translates, using a MAP 114 containing information on the patient's psychophysical test results, the voice pitch information into a pattern of electrical stimulation on two electrodes that are stimulated sequentially. The data so translated is sent by the patient coil 115 to the implanted receiver stimulator unit RSU 3 (FIG. 2).

Three bandpass filters 116, 117 and 118 also receive the audio signal from microphone 110 before it is applied to the speech feature extractor 112, and separate the signal into three components of different frequencies, a 2000–2800 Hz signal in band 3, a 2800–4000 Hz signal in band 4, and 4000–8000 Hz signal in band 5. The signals from bands 3, 4 and 5 are lead to the encoder 113 and mapping of these signals is done in a manner similar to that for the first and second formants, and translation of the resulting pattern of electrical stimulation to the appropriate electrodes takes place, as discussed earlier herein The automatic gain control amplifier 111 is used to control the amplitude of the signal fed to the filters 116 and 117. Since filter 118 is only used for unvoiced parts of the speech signal, its amplitude is never very great and, therefore, the signal does not require automatic gain control. Accordingly, amplifier 119 does not have automatic gain control provisions incorporated therein.

To summarize, the psychophysical measurements that are made using the DPS software provide the information for translating the extracted acoustic input into patient-specific stimulation parameters. Threshold (T) and maximum (C) levels for electrical stimulation are measured for each electrode pair. These values are stored in the MAP. They determine the relationship between the incoming acoustic signal amplitude and the stimulation level for any given electrode pair.

Inside the speech processor a random access memory stores a set of number tables, referred to collectively as a MAP. The MAP determines both stimulus parameters for F1, F2 and bands 3–5, and the amplitude estimates. The encoding of the stimulus parameters follows a sequence of distinct steps. The steps may be summarized as follows:

1. The first formant frequency (F1) is converted to a number based on the dominant spectral peak in the region between 280–1000 Hz.

2. The F1 number is used, in conjunction with one of the MAP tables, to determine the electrode to be stimulated to represent the first formant. The indifferent electrode is determined by the mode.

3. The second formant frequency (F2) is converted to a number based on the dominant spectral peak in region between 800–4000 Hz.

4. The F2 number is used, in conjunction with one of the MAP tables to determine the electrode to be stimulated to represent the second formant. The indifferent electrode is determined by the mode.

5. The amplitude estimates for bands 3, 4 and 5 are assigned to the three default electrodes 7, 4 and 1 for bands 3, 4 and 5, respectively, or such other electrodes that may be selected when the MAP is being prepared.

6. The amplitude of the acoustic signal in each of the frequency bands is converted to a number ranging from 0–150. The level of stimulation that will be delivered is determined by referring to a set MAP tables that relate acoustic amplitude (in range of 0–150) to stimulation level for the specific electrodes selected in steps 2, 4 and 5, above.

7. The data are further encoded in the speech processor and transmitted to the receiver/stimulator. It, in turn, decodes the data and sends the stimuli to the appropriate electrodes. Stimulus pulses are presented at a rate equal to F0 during voiced periods and at a random aperiodic rate (typically 200 to 300 Hz) during unvoiced periods.

It will be apparent from the foregoing description that the multi-spectral peak speech coding scheme of the present invention provides all of the information available in the prior art F0F1F2 scheme, while providing additional information from three high frequency band pass filters. These filters cover the following frequency ranges: 2000 to 2800 Hz, 2800 to 4000 Hz and 4000 to 8000 Hz. The energy within these ranges controls the amplitude of electrical stimulation of three fixed electrode pairs in the basal end of the electrode array. Thus, additional information about high frequency sounds is presented at a tonotopically appropriate place within the cochlea.

The overall stimulation rate remains as F0 (fundamental frequency or voice pitch) but in the scheme of the present invention four electrical stimulation pulses occur for each glottal pulse. This compares with the prior F0F1F2 strategy in which only two pulses occur per voice pitch period. In the new coding scheme, for voiced speech sounds, the two pulses representing the first and second formant are still provided, and additional stimulation pulses occur representing energy in the 2000–2800 Hz and the 2800–4000 Hz ranges.

For unvoiced phonemes, yet another pulse representing energy above 4000 Hz is provided while no stimulation for the first formant is provided, since there may be no energy in this frequency range. Stimulation occurs at a random pulse rate of approximately 260 Hz, which is about double that used in the earlier strategy.

It will be further apparent from the foregoing description that this invention provides an improved cochlear implant system which overcomes various of the problems associated with earlier cochlear implant systems. The use of a multi-spectral peak speech coding strategy in accordance with this invention provides the user of the implant system with significantly improved speech recognition, even in the presence of moderate levels of background noise. In addition improved recognition of phonemes and environmental sounds are provided by this invention.

While a particular embodiment of this invention has been shown and described, it will be obvious to those skilled in the art that various changes and modifications may be made without departing from this invention in its broader aspects, and it is, therefore, aimed in the appended claims to cover all such changes and modifications as fall within the true spirit and scope of this invention.

What is claimed is:

1. A method of processing in a speech processor an audio signal, received from a microphone coupled to the speech processor, to produce signals for stimulating a patient-implantable, tissue-stimulating, multi-channel electrode array having apical and basal regions therein and being configured to be positioned in a cochlea from a corresponding apical region of the cochlea to a corresponding basal region of the cochlea, said method comprising the steps of:

selecting a first dominant spectral peak from said audio signal from a frequency band of between 280 Hz and 1000 Hz and stimulating at least one electrode in the apical region of said electrode array corresponding to said first peak;

selecting a second dominant spectral peak from said audio signal from a frequency band of between 800 Hz and 4000 Hz and stimulating at least one electrode in the basal region of said electrode array corresponding to said second peak; and, extracting spectral information in at least one region of a spectrum of said audio signal and stimulating at least a first additional electrode in the basal region of said electrode array corresponding to said extracted spectral information.

2. A method of processing an audio signal as claimed in claim 1, including the further steps of stimulating second and third additional electrodes in the basal region of said electrode array, said first, second and third electrodes being stimulated using spectral energy derived from said audio signal in respective audio frequency regions of 2000 to 2800 Hz, 2800 to 4000 Hz and above 4000 Hz.

3. A method of speech coding in a speech processor an audio signal, received from a microphone coupled to the speech processor, to produce signals for stimulating a patient-implantable, tissue-stimulating, multi-channel electrode array having apical and basal regions therein and being configured to be positioned in a cochlea from a corresponding apical region of the cochlea to a corresponding basal region of the cochlea, said method comprising the steps of:

providing to a patient through said electrode array initial high frequency information from said audio signal corresponding to a normal second format peak F2 occurring within a normal range of about 800 Hz to 4000 Hz;

band pass filtering said audio signal into a plurality of bands within and beyond said normal range of said second format frequency peak F2; and providing to the patient through said array additional high frequency information from said bands.

4. The method of claim 3, including the further steps of encoding said information derived from said audio signal into sequential pulses and applying said sequential pulses to selected electrodes of said electrode array.

* * * * *